(12) United States Patent
Ohtsu et al.

(10) Patent No.: US 7,695,774 B2
(45) Date of Patent: Apr. 13, 2010

(54) TITANIUM OXIDE PHOTOCATALYST THIN FILM AND PRODUCTION METHOD OF TITANIUM OXIDE PHOTOCATALYST THIN FILM

(75) Inventors: Shigemi Ohtsu, Ashigarakami-gun (JP); Tatsuya Maruyama, Ashigarakami-gun (JP); Eiichi Akutsu, Ashigarakami-gun (JP); Kazuhito Hashimoto, Yokohama (JP)

(73) Assignees: Fuji Xerox Co., Ltd., Tokyo (JP); Toudai TLO, Ltd., Tokyo (JP)

( * ) Notice: Subject to any disclaimer, the term of this patent is extended or adjusted under 35 U.S.C. 154(b) by 1016 days.

(21) Appl. No.: 11/125,260

(22) Filed: May 10, 2005

(65) Prior Publication Data
US 2005/0197248 A1    Sep. 8, 2005

Related U.S. Application Data

(62) Division of application No. 10/352,200, filed on Jan. 28, 2003, now abandoned.

(30) Foreign Application Priority Data
Jan. 31, 2002   (JP) .................... 2002-23175

(51) Int. Cl.
  B05D 3/06    (2006.01)
  B05D 3/02    (2006.01)
  B05D 5/06    (2006.01)
  C23C 16/48   (2006.01)
  C23C 16/56   (2006.01)
  C23C 14/08   (2006.01)
  C23C 14/28   (2006.01)
  C23C 14/58   (2006.01)

(52) U.S. Cl. ............... 427/553; 427/555; 427/558; 427/559; 427/583; 427/586; 427/596

(58) Field of Classification Search .............. None
See application file for complete search history.

(56) References Cited

U.S. PATENT DOCUMENTS

| | | | |
|---|---|---|---|
| 5,579,162 A | * | 11/1996 | Bjornard et al. ............ 359/580 |
| 6,013,372 A | * | 1/2000 | Hayakawa et al. ........ 428/411.1 |
| 6,037,289 A | | 3/2000 | Chopin et al. |
| 6,090,489 A | | 7/2000 | Hayakawa et al. |

(Continued)

FOREIGN PATENT DOCUMENTS

CN    1209153 A    2/1999

(Continued)

OTHER PUBLICATIONS

Machine translation of JP 11-19,520.*

Primary Examiner—Marianne L Padgett
(74) Attorney, Agent, or Firm—Oliff & Berridge, PLC

(57) ABSTRACT

The present invention provides a titanium oxide photocatalytic thin film having a surface layer containing silicon oxide and titanium oxide and a production method for producing a titanium oxide photocatalytic thin film having a surface layer containing silicon oxide and titanium oxide and comprising a step of radiating excimer beam to the titanium oxide thin film while heating substrate on which the titanium oxide thin film is disposed in vacuum or gas atmosphere in the presence of a silicon-including compound.

17 Claims, 6 Drawing Sheets

U.S. PATENT DOCUMENTS

| | | | |
|---|---|---|---|
| 6,103,363 A | 8/2000 | Boire et al. | |
| 6,185,034 B1 * | 2/2001 | Nakamura et al. | 359/265 |
| 6,414,213 B2 | 7/2002 | Ohmori et al. | |
| 6,572,964 B2 * | 6/2003 | Tanaka et al. | 428/328 |
| 6,576,344 B1 * | 6/2003 | Doushita et al. | 428/426 |
| 6,677,063 B2 * | 1/2004 | Finley | 428/701 |
| 6,694,880 B1 * | 2/2004 | Mori et al. | 101/467 |
| 6,793,980 B2 * | 9/2004 | Ohtsu et al. | 427/558 |
| 6,816,297 B1 * | 11/2004 | Tonar et al. | 359/265 |
| 6,887,816 B2 * | 5/2005 | Tanaka et al. | 502/100 |
| 7,132,157 B2 * | 11/2006 | Oswald et al. | 428/325 |
| 2001/0014396 A1 | 8/2001 | Tanaka et al. | |
| 2002/0045073 A1 | 4/2002 | Finley | |
| 2003/0134128 A1 | 7/2003 | Oswald et al. | |
| 2006/0225999 A1 * | 10/2006 | Fukawa et al. | 204/192.26 |
| 2008/0017502 A1 * | 1/2008 | Fukawa et al. | 204/192.12 |

FOREIGN PATENT DOCUMENTS

| | | | | |
|---|---|---|---|---|
| JP | 2-130914 | * | 5/1990 | 117/43 |
| JP | A 5-92192 | | 4/1993 | |
| JP | A 6-315614 | | 11/1994 | |
| JP | A 7-102678 | | 4/1995 | |
| JP | A-08-165113 | | 6/1996 | |
| JP | A 9-57912 | | 3/1997 | |
| JP | A-09-059042 | | 3/1997 | |
| JP | A 9-129012 | | 5/1997 | |
| JP | A-10-85610 | | 4/1998 | |
| JP | A-10-278168 | | 10/1998 | |
| JP | A-10-329261 | | 12/1998 | |
| JP | 11-19520 | * | 1/1999 | |
| JP | A-2000-017488 | | 1/2000 | |
| JP | A-2000-176281 | | 6/2000 | |
| JP | A-2001-38221 | | 2/2001 | |
| JP | 2001-91724 | * | 4/2001 | |
| JP | A 2001-98187 | | 4/2001 | |
| JP | A-2001-231649 | | 8/2001 | |
| JP | A-2001-335343 | | 12/2001 | |
| JP | A-2002-023356 | | 1/2002 | |

* cited by examiner

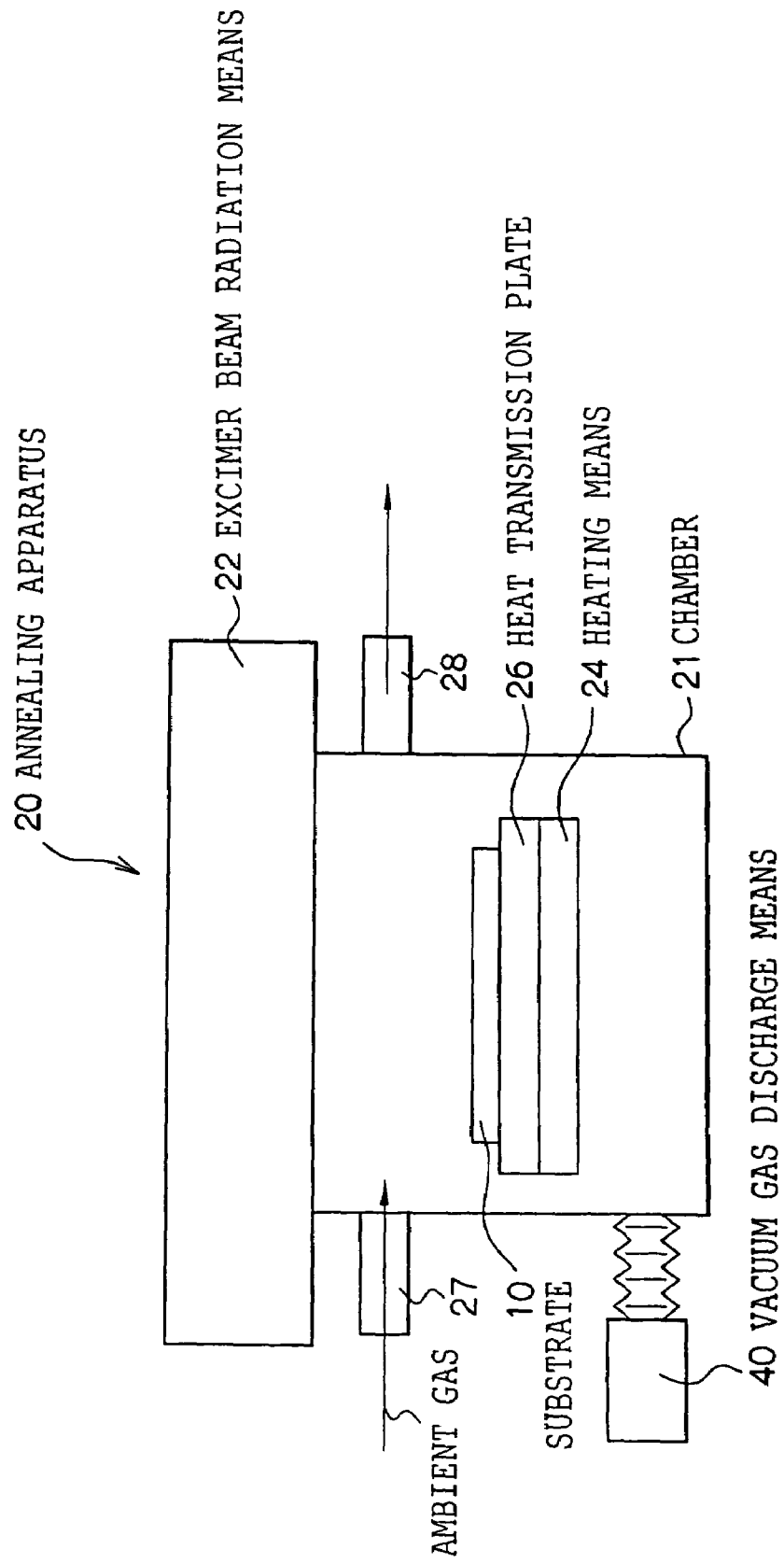

TITANIUM OXIDE PHOTOCATALYST THIN FILM AND PRODUCTION METHOD OF TITANIUM OXIDE PHOTOCATALYST THIN FILM

This is a Divisional of application Ser. No. 10/3 52,200 filed on Jan. 28, 2003, now abandoned. The entire disclosure of the prior application is hereby incorporated by reference herein in its entirety.

BACKGROUND OF THE INVENTION

1. Field of the Invention

The present invention relates to a titanium oxide photocatalyst thin film having photocatalytic activities such as antibacterial action, anti-pollution, air purification, ultra high hydrophilicity and the like on a substrate and its production method.

2. Description of the Related Art

In recent years, a photocatalyst or a photosemiconductor having the photocatalytic function or the photovoltaic function has been drawing attention. There are many application methods have been proposed, for example, titanium oxide, which is a photocatalyst (photosemiconductor), is said to oxidize and decompose organic stains adhering to surface, nitrogen oxide (NOx), sulfur oxide (SOx), air pollutants such as malodorous substances, bacteria, and the like owing to the oxidation reaction based on the photocatalytic reaction and as an practical application example, a method for removing air pollutants under sunray (Japanese Patent Application Laid-Open (JP-A) No. 6-315614) by attaching a titanium oxide photocatalyst to walls of buildings, a method for disinfecting bacteria (JP-A No. 7-102678) by attaching a titanium oxide catalyst to walls, handrails and the like in a hospital, a method for decomposing pollutants in water (JP-A No. 5-92192) by dispersing a titanium oxide catalyst powder in wastewater and radiating light of a ultraviolet lamp, a method for lessening the cleaning and maintenance work of a fluorescent lamp or luminaire (JP-A No. 9-129012) owing to self-cleaning reaction, and the like.

Further, based on its photoreaction, a photocatalytic thin film is known to have surface made highly hydrophilic and a variety of applications for anticlouding of mirrors (of bathrooms, automobiles), lens, glass windows and the like are supposed to be possible.

Further, when the photocatalytic thin film is disposed on the surfaces of building outer walls, automotive glass, and window glass, based on the hydrophilicity of the film surfaces, besides that hydrophobic stains are hard to adhere to, even if stains adhere, they are decomposed and owing to the hydrophilicity of the forgoing photocatalytic thin film, the stains or their decomposed substances are known to have self-cleaning function that they are easily washed out by rain or washing with water.

With respect to the foregoing photocatalytic thin film, the following methods are generally well known: a titanium compound such as a titanium alkoxide, a titanium acetate and the like are hydrolyzed and then applied to the surface of a substrate and dried and after that, sintered at 500° C. or higher to obtain an anatase type titanium oxide film; after an amorphous titanium oxide layer is formed by a deposition method, the obtained amorphous titanium oxide layer is annealed at 400° C. or higher to form an anatase type titanium oxide-containing layer; the surface of metal titanium is oxidized at 500° C. or higher to crystallized the surface; while a substrate being heated at 250° C. or higher, an anatase type titanium oxide film is obtained by RF sputtering method.

The foregoing photocatalytic thin film is provided with its hydrophilicity upon receiving ultraviolet rays. However, the hydrophilicity has a characteristic in that the hydrophilicity is weakened if it is kept in a dark place for about a weak. In order to improve the defects, JP-A No. 2001-98187 discloses a photocatalytic hydrophilic member bearing on the substrate surface, a surface layer including a photocatalytic titanium oxide coated with an alkali silicate and an inorganic acid particle (silica or the like) with an isoelectric point of pH 5 or lower and when an alkali silicate other than the photocatalyst is contained in the surface layer, the surface is provided with hydrophilicity as high degree as 20° or lower water wettability angle and the hydrophilicity retention property in the case of storage in a dark place is improved. Further, JP-A No. 9-57912 discloses a composite material having good water hydrophilicity retention property for a long duration even in the case of storage in the dark by forming a hydrophilicity layer such as silica or silicone resin (containing hydroxy group) on a photocatalytic semiconductor thin film.

All these methods are either a titanium oxide particle or a titanium oxide thin film coated with silica or the like on the surface and owing to the surface coating film existence, they have a problem that the photocatalytic capability such as an organic decomposition activity by the titanium oxide particle or the titanium oxide thin film is deteriorated. Further, in order to increase the photocatalytic activity, a method for solving the problem is that the photocatalytic film is thickened, however the method has a disadvantage that interference coloration occurs since titanium oxide has a high refractive index and therefore, the thickness cannot be thickened so much.

SUMMARY OF THE INVENTION

Taking the above-mentioned problems into consideration, the present invention aims to provide a photocatalytic thin film having retainable photocatalytic activity even in the case of storage in the dark and its production method.

Providing the following titanium oxide photocatalytic thin film and the production method of the same can solve the above-mentioned problems.

A first aspect of the invention provides a titanium oxide photocatalytic thin film comprising a surface layer including silicon oxide and titanium oxide.

A second aspect of the invention provides the titanium oxide photocatalytic thin film, according to the first aspect, wherein the titanium oxide photocatalytic thin film is disposed on a substrate.

A third aspect of the invention provides the titanium oxide photocatalytic thin film, according to the first aspect, wherein the titanium oxide photocatalytic thin film is disposed on a substrate and at least one of a reflection prevention film and a protection film is disposed between the titanium oxide photocatalytic thin film and the substrate.

A fourth aspect of the invention provides the titanium oxide photocatalytic thin film, according to the first aspect, wherein the film thickness of the titanium oxide photocatalytic thin film is in a range from 10 to 120 nm or 180 to 230 nm.

A first aspect of the invention provides a production method of a titanium oxide photocatalytic thin film comprising a surface layer including silicon oxide and titanium oxide, the production method comprising the steps of: forming a titanium oxide thin film on a substrate; and radiating excimer beam to the titanium oxide thin film while heating the substrate in a vacuum or a gas atmosphere in the presence of a compound, which includes silicon.

A second aspect of the invention provides the production method of a titanium oxide photocatalytic thin film, according to the first aspect, wherein the titanium oxide photocatalytic thin film is disposed on a substrate.

A third aspect of the invention provides the production method of a titanium oxide photocatalytic thin film, according to the first aspect, wherein the titanium oxide photocatalytic thin film is disposed on a substrate and at least one of a reflection prevention film and a protection film is disposed between the titanium oxide photocatalytic thin film and the substrate.

A fourth aspect of the invention provides the production method of a titanium oxide photocatalytic thin film, according to the first aspect, wherein the film thickness of the titanium oxide photocatalytic thin film is in a range from 10 to 120 nm or 180 to 230 nm.

A fifth aspect of the invention provides the production method of a titanium oxide photocatalytic thin film, according to the first aspect, wherein the heating temperature of the substrate is in a range from 50° C. to 230° C.

A sixth aspect of the invention provides the production method of a titanium oxide photocatalytic thin film, according to the first aspect, wherein the substrate comprises a plastic substrate and the substrate heating temperature is in a range from room temperature to the heat resistant temperature of the plastic substrate.

A seventh aspect of the invention provides the production method of a titanium oxide photocatalytic thin film, according to the first aspect, further comprising the step of disposing a reflection prevention film between the titanium oxide thin film and the substrate.

An eighth aspect of the invention provides the production method of a titanium oxide photocatalytic thin film, according to the seventh aspect, wherein the reflection prevention film comprises an inorganic oxide thin film.

A ninth aspect of the invention provides the production method of a titanium oxide photocatalytic thin film, according to the seventh aspect, wherein the refractive index of the reflection prevention film is within a range from 1.5 to 2.3.

A tenth aspect of the invention provides the production method of a titanium oxide photocatalytic thin film, according to the seventh aspect, wherein the refractive index of the reflection prevention film is between the refractive index of the substrate and the refractive index of the titanium oxide photocatalytic thin film; and the optical film thickness, as expressed by a product of the film thickness and the refractive index of the reflection prevention film, is one of ¼ of a wavelength and a whole number multiple of ¼ of the wavelength, wherein the wavelength is in the vicinity of the center of the visible light range.

An eleventh aspect of the invention provides the production method of a titanium oxide photocatalytic thin film, according to the seventh aspect, wherein the optical film thickness of the reflection prevention film, as expressed by a product of the film thickness and the refractive index of the reflection prevention film, is in a range from 110 nm to 160 nm or 330 nm to 480 nm.

An twelfth aspect of the invention provides the production method of a titanium oxide photocatalytic thin film, according to the first aspect, further comprising a step of disposing a protection film between the titanium oxide thin film and the substrate wherein the substrate comprises a plastic substrate.

A thirteenth aspect of the invention provides the production method of a titanium oxide photocatalytic thin film, according to the twelfth aspect, wherein the protection film comprises an inorganic oxide thin film.

A fourteenth aspect of the invention provides the production method of a titanium oxide photocatalytic thin film, according to the thirteenth aspect, wherein the inorganic oxide thin film is selected from a group consisting of an amorphous titanium oxide thin film, $SnO_2$ thin film, a $SiO_2$ thin film, and an ITO thin film.

A fifteenth aspect of the invention provides the production method of a titanium oxide photocatalytic thin film, according to the twelfth aspect, wherein the refractive index of the protection film is in a range from 1.4 to 2.3.

A sixteenth aspect of the invention provides the production method of a titanium oxide photocatalytic thin film, according to the twelfth aspect, wherein the refractive index of the protection film is between the refractive index of the substrate and the refractive index of the titanium oxide photocatalytic thin film; and the optical film thickness, as expressed by a product of the film thickness and the refractive index of the protection film, is one of ¼ of a wavelength and a whole number multiple of ¼ of the wavelength, wherein the wavelength is in the vicinity of the center of the visible light range.

A seventeenth aspect of the invention provides the production method of a titanium oxide photocatalytic thin film, according to the twelfth aspect, wherein the optical film thickness of the protection film is in a range from 10 nm to 160 nm or 330 nm to 480 nm.

An eighteenth aspect of the invention provides the production method of a titanium oxide photocatalytic thin film, according to the first aspect, wherein the titanium oxide thin film is disposed by a method selected from a group consisting of a sputtering method, an electron beam deposition method, and an ion plating method.

BRIEF DESCRIPTION OF THE DRAWINGS

FIG. 6 is a conceptual diagram showing an apparatus for carrying out a production method of the invention. In FIG. 6, the reference numeral 10 represents a substrate, 20 represents an annealing apparatus, 21 represents a chamber, 22 represents excimer beam radiation means, 24 represents heating means, and 40 represents vacuum discharge means.

DESCRIPTION OF THE PREFERRED EMBODIMENTS

Figure 1A:
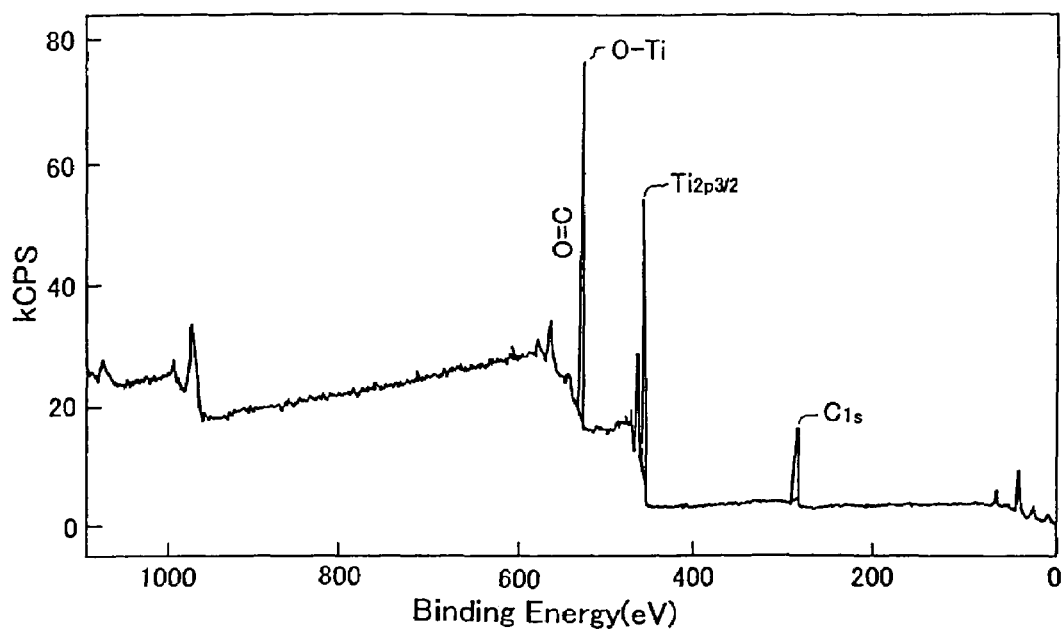
FIG. 1A is a graph showing an XPS measurement result of a titanium oxide thin film before the treatment of Example 1.

A production method of a titanium oxide photocatalytic thin film of the invention comprises a step of radiating excimer beam to a titanium oxide thin film while heating the substrate bearing a titanium oxide thin film in vacuum or a gas atmosphere in the presence of a silicon compound. Unlike those produced by the above-mentioned conventional methods for coating titanium oxide surface with silica, a photocatalytic thin film obtained by this method does not cause photocatalytic activity deterioration and maintains a low contact angle to water. Further, since the titanium oxide photocatalytic thin film obtained by the method has its activity, even if the film thickness is made thin, sufficiently high photocatalytic activity can be obtained. Accordingly, interference color can be eliminated from the light attributed to a high refractive index of titanium oxide and high transparency in the visible ray region. Further, this method has an advantage that the treatment time can be short and any large scale apparatus is required, as compared with a conventional method.

The titanium oxide photocatalytic thin film obtained by this method is characterized in that the surface layer contains silicon oxide and titanium oxide. The layer containing silicon oxide and titanium oxide includes a surface layer of a mixture containing silicon oxide and titanium oxide, a surface layer of a mixture containing a compounded oxide of silicon oxide and titanium oxide. Owing to such a surface layer of the invention, the titanium oxide photocatalytic thin film is provided with excellent ultra high hydrophilicity and photocatalytically active characteristic as described above.

As the substrate to be employed for a production method of the invention, a glass substrate, a plastic substrate such as a plastic film, sheet, plate or the like, a ceramic substrate such as a ceramic sheet, ceramic plate or the like, and the like can be exemplified without any limit. As the plastic substrate, for example, films, sheets, or plates of plastics of polyethylene terephthalate, polyethylene naphthalate, polyether ether ketone, polyether sulfone, polysulfone, polyether imide, polyether ketone, polyphenylene sulfide, polyallylate, polyimide, polycarbonate, Arton and the like can be exemplified and they are preferably flexible based on the applications.

To form the titanium oxide thin film with a high photocatalytic effect, since the heating temperature of the titanium oxide thin film is preferable to be a relatively high, in the case a plastic substrate is used as a substrate, it is preferable to use a plastic substrate with higher heat resistance. As the heat resistant plastic substrate, polyimide (heat resistant temperature 331° C.), polycarbonate (PC) (heat resistant temperature 205° C.), polyether sulfone (PES) (heat resistant temperature 223° C.), polysulfone (PS) (heat resistant temperature 190° C.), Norbornene resin (trade name; Arton) (heat resistant temperature 171° C.). Specially, heat resistant PC and PES have high transparency and heat resistance to a temperature as high as about 220 degree and less optical anisotropy.

In the invention, the phrase, heat resistant temperature of a plastic substrate, means the glass transition temperature of about 100 to 230° C.

In the case a plastic substrate is used as a substrate, the thickness is preferably 30 to 300 µm, further preferably 80 to 230 µm.

In the case that a photocatalytic thin film to be produced by the method of the invention is used for anticlouding or stainproofing articles which reflect light or transmit light, the substrate is also required to a light transmission property (hereinafter, simply referred to as transparency in some cases).

The titanium oxide thin film in the invention may include any of an amorphous titanium oxide thin film, a titanium oxide thin film in which an amorphous portion and a crystalline portion are mixed, or a crystalline titanium oxide thin film. By heating a titanium oxide thin film containing an amorphous portion while excimer beam being radiated, crystallization and formation of the foregoing surface layer are carried out. Further, by carrying out the treatment of the invention to the crystalline titanium oxide thin film, the foregoing surface layer formation is carried out.

Further, it is general that as the film thickness of the titanium oxide thin film can be increased more, the photocatalytic activity is increased more, however interference coloration is caused owing to the high refractive index of titanium oxide. However, according to the production method of the invention, even if the film thickness of the titanium oxide thin film is thin, sufficiently high photocatalytic activity can be obtained.

In the case the photocatalytic thin film is used for an application for which transparency is required, the titanium oxide thin film is also required to be transparent and generally, taking the center wavelength $\lambda$ of the visible light and the refractive index n of anatase type titanium oxide into consideration, the film thickness of the titanium oxide thin film is preferably $\lambda/(2 \times n)$ or shorter or whole number multiple of $\lambda/(2 \times n)$. Supposing that the foregoing the center wavelength is 550 nm and the refractive index of the anatase type titanium oxide is 2.53, $\lambda/(2 \times n)=109$ nm and therefore, the film thickness of titanium oxide is preferable to be 110 nm or thinner or about 220 nm. However, since the transparency to a certain degree can be obtained even if the film thickness is slightly different from those in the entire visible light wavelength region, practically in a range from 10 to 120 nm and 180 nm to 230 nm, transparency can be obtained without appearance of the interference color.

In the production method of the invention, as a method for forming a titanium oxide thin film, a sputtering method, an RF sputtering method, an EB deposition method, an ion plating method and the like can be employed.

In the case of producing a titanium oxide thin film on a plastic substrate, film formation is preferably carried out by the sputtering method or the RF sputtering method by which the film formation is made possible even at a relatively low temperature, for example, a heat resistant temperature (230° C. or lower) of those with good transparency among a variety of presently well known plastics and scarcely accompanied with damages on the substrate.

As the compound which includes silicon (the silicon-including compound) made coexisting in the treatment of the invention, either inorganic or organic compound is possible and more practically, a —Si—O-including compound can be exemplified and glass, quartz, silicon and the like are examples of the inorganic compound and silicone resin, silicone rubber, silicone oil, polysilane, silane gas and the like are examples of the organic compound.

The foregoing silicon-including compound is preferably put in a system where the treatment is carried out and arranged so as to radiate excimer beam to the silicon-including compound itself.

For example, while the treatment system in the production method of the invention being covered with quartz glass (for example, in the case of carrying out a production method of the invention in a quartz bell jar), the treatment (heating and excimer beam radiation) of the invention may be carried out or as a member of a production apparatus to be employed for the production method of the invention, a member made of silicone resin is employed, so that the surface layer of the titanium oxide photocatalytic thin film can be made a layer including silicon oxide and titanium oxide as described above.

Although it depends on the heating time, the heating temperature of the substrate is high enough to be a room temperature (25° C.) or higher, preferably 50° C. or higher, in order to convert the amorphous state to crystalline or polycrystalline state and obtain a titanium oxide thin film having a high photocatalytic effect and at the same time form the surface layer as described above. In order to increase the crystallinity and efficiently form the surface layer, the heating temperature is better to be high. Accordingly, the upper limit temperature of heating is not particularly limited, however in terms of the heating method selection, heating temperature control, energy loss and the like, it is preferably about 300° C., more preferably about 250° C. In order to efficiently increase the crystallinity degree, and to make the heating condition adequate, it is preferable to heat a substrate to 100 to 200° C.

In the case the substrate is a plastic substrate, the heating upper limit temperature is the heat resistant temperature of the plastic substrate. What the heating resistant temperature of the plastic substrate is, in the case of the foregoing plastic substrates, at highest about 230° C. Further, from the above described viewpoint, even in the case of the plastic substrate, heating is preferably at about 100 to 200° C. (nevertheless, in the case the heat resistant temperature of the plastic substrate is at 200° C. or lower, it is in a range up to its heat resistant temperature).

For the excimer beam radiation, a commonly sold excimer lamp is preferable to be employed. Further, as the wavelength of excimer beam is shorter, the beam energy is more intense and UV rays with wavelength of 365 nm or shorter, preferably 308 nm or shorter, are preferable to be employed (for example, UV rays of 308 nm, 202 nm, 172 nm).

Even the excimer beam radiation dose of about 1 to 50 mW/cm$^2$ can sufficiently convert a titanium oxide thin film to a photocatalytic thin film. Further, it is general that as the excimer beam radiation time is longer, a titanium oxide thin film can be converted into a photocatalyst thin film better. Although depending on the excimer beam wavelength, beam intensity, heating temperature, in the case of using an excimer lamp with a wavelength of 172 nm, beam intensity of 10 mW/cm$^2$, and a heating temperature of 125° C., the radiation time is proper to be 30 seconds to at longest 20 minutes. Further, although depending on whether emphasis of the treatment of the invention is put on both crystallization of an amorphous titanium oxide and formation of the foregoing surface layer or on only formation of the surface layer, the beam radiation time of the excimer lamp is sufficient to be about 15 minutes in the former case and about 1 minute in the latter case.

The ambient atmosphere at the time of heating and excimer beam radiation is vacuum or a gas atmosphere. The term, vacuum, generally means the vacuum degree of about $10^{-2}$ Pa, however taking other conditions into consideration, it can be properly selected. As the gas atmosphere, for example, one or more kinds of gases such as hydrogen gas, nitrogen gas, ammonia gas, rare gas such as He, Ne, Ar, and carbon monoxide can be employed. The gas atmosphere preferably reductive atmosphere containing hydrogen gas and more preferably atmosphere having a low oxygen partial pressure. In order to lower the oxygen partial pressure, the heating temperature of a titanium oxide thin film can be decreased.

For example, in the case the treatment of the invention is carried out in a highly pure nitrogen gas reductive atmosphere containing 2 to 5% (explosion limit or lower) of hydrogen (in the case of using an apparatus having a capacity of, for example, 1 L, the flow rate is controlled to be 0.5 to 2 L/min), amorphous state is converted to be polycrystalline and lattice defects of oxygen is caused and thus carrier concentration of the titanium oxide thin film is increased to improve the photoelectric properties and the photocatalytic properties. The pressure of the reductive atmosphere may be normal pressure (atmospheric pressure) and may be decreased pressure.

In the case a layer containing silicon oxide and titanium oxide is formed, the photocatalytic properties such as ultra high hydrophilicity and the like can be well retained even in a dark place and kept for 3 months or longer.

Further, in the case the photocatalytic thin film produced by the method of the invention is required to have a light transmissive property, a reflection prevention film is disposed on a light transmissive substrate and a titanium oxide thin film is disposed on the reflection prevention film or the optical film thickness of the titanium oxide thin film is controlled to be a specified thickness, so that light reflection between the light transmissive substrate and the titanium oxide thin film can be prevented from occurring and the thin film with remarkably high light transmittance can be obtained.

The refractive index of the reflection prevention film can be controlled to be in a range from 1.5 to 2.3.

The foregoing reflection prevention film can be composed of, for example, an inorganic oxide dielectric.

As the inorganic oxide dielectric to be employed for the reflection prevention film, there are $SnO_2$, ITO, $CeF_3$, ZnS, MgO, $Gd_2O_3$, $Sc_2O_3$, $ZrO_2$, SiO, $HfO_2$, $CeO_2$, and the like. Specially, $ZrO_2$ is generally used as a material of a dielectric thin film with a high refractive index. The reflection prevention film of an inorganic oxide dielectric can be easily formed to be thin by a sputtering method, a RF sputtering method, an electron beam deposition method and the like.

In the case the reflection prevention film is a monolayer, the refractive index n is preferably to be between the refractive index of the foregoing light transmissive substrate and the refractive index of the titanium oxide photocatalytic thin film and the optical film thickness represented by a product of the film thickness and the reflective index of the protection film is preferably ¼ of wavelength in the vicinity of the visible ray range or a whole number multiple of ¼ of the wavelength in terms of the elimination of light reflection between the light transmissive substrate and the titanium oxide thin film.

For example, in the case a substrate is of glass with 1.5 refractive index 1.5 and a titanium oxide photocatalytic thin film of titanium oxide with 2.5 refractive index, assuming the center wavelength of visible light rays is 550 nm, a film having a refractive index in the middle of them, about 1.8 to 2.0, for example a $ZrO_2$ with a refractive index of 2.06, and having a film thickness of 69 nm [550/(4×2.06)=69] or its whole number multiple is effective to be employed as the reflection prevention film. Practically, such a film with a film thickness 63 nm to 75 nm may be usable. Further in the case of ITO with a refractive index of 1.9, an ITO film with a film thickness of about 72 nm [550/(4×1.9)=72] or its whole number multiple is effective to be employed. Practically, such a film with a film thickness of 66 nm to 78 nm may be usable. However, since a practical refractive index of a reflection prevention film differs depending on the film formation conditions, it is required to determine the film thickness depending on the alteration.

Generally, if the optical film thickness, the product of the film thickness of the reflection prevention film and the refractive index, is within a range 110 nm to 160 nm or within a range from 330 nm to 480 nm, reflection can be effectively prevented.

Further, in place of formation of the reflection prevention film on a substrate, occurrence of light reflection between a titanium oxide photocatalytic thin film and a substrate can be prevented by controlling the optical film thickness represented by the product of the film thickness and the refractive index of the titanium oxide thin film to be ½ of wavelength in the vicinity of the center of the visible light range or shorter or to be whole number multiple of ½ of wavelength in the vicinity of the center of the visible light range.

As one example, assuming the center wavelength of visible light rays is 550 nm, in the case titanium oxide with a refractive index of 2.5 is used as a titanium oxide photocatalytic thin film, for example, the thickness of the titanium oxide thin film may be controlled to be not more than about 550/(2×2.5)=110 (nm) or its whole number multiple. (It is not necessary to strictly adjust to be the numeral value).

Further, in the case a plastic substrate is used as a substrate, the plastic substrate is sometimes deteriorated owing to the photocatalytic reaction of the titanium oxide. Accordingly, to suppress the deterioration of the photocatalytic film, it is preferable to form a protection film of an oxide compound between the plastic substrate and the titanium oxide photocatalytic film. The refractive index of the protection film is proper to be in a range from 1.4 to 2.3 from a viewpoint of the transparency.

Practically, a $ZrO_2$ thin film, an ITO thin film and the like can be used. In this case, the protection film may be used as the foregoing reflection prevention film. Accordingly, as the protection film, those similar to a $ZrO_2$ thin film, a $SnO_2$ thin film, a $SiO_2$ thin film, an ITO thin film as the foregoing reflection prevention film may be use.

Besides, an amorphous titanium oxide thin film may be used as the protection film. Since the film thickness of the amorphous titanium oxide thin film (about 2.5 refractive index) can be controlled to be several 10 nm, no practical effect is caused on the transparency.

Further, the refractive index of the foregoing protection film is preferably between the refractive index of the foregoing substrate and the refractive index of the titanium oxide photocatalytic thin film and the optical film thickness represented by a product of the film thickness and the reflective index of the protection film is preferably ¼ of wavelength in the vicinity of the visible ray range or its whole number multiple in terms of the prevention of light transmission property even if the protection film is formed.

Generally, if the optical film thickness of the protection film is in a range from 10 nm to 160 nm or in 330 nm to 480 nm, the protection film performs the function as a protection film without deteriorating the transparency.

A photocatalytic thin film of the invention may be in form of a composite material, as described above, of a substrate and a reflection prevention film, a protection film layered thereon.

In the case the substrate of the foregoing composite material is a flexible plastic substrate, it may be rolled like a roll and may be advantageously used for the purpose of stain prevention of outer walls of buildings and the like. Further, the substrate of the foregoing composite material is a light transmissive plastic substrate or a light transmissive flexible plastic substrate, the material may be advantageously used for anticlouding and stainproofing for glass windows, mirrors and the like.

Further, in the foregoing composite material, if a reflection prevention film as described above is disposed between the substrate and the titanium oxide photocatalytic thin film, the light transmission property is improved and therefore, the material is especially preferable for articles which reflect light or transmit light.

Further, in the case the substrate is a plastic substrate, formation of a protection layer between the substrate and the titanium oxide photocatalytic thin film prevents undesirable effects of the activity of the photocatalytic thin film on the substrate, so that even if the composite material is in environments under which the material is exposed to light for a long term, the plastic substrate can be prevented from deterioration.

Figure 5A:
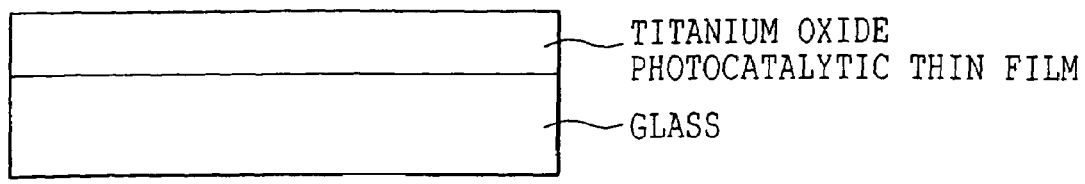
FIGS. 5A, 5B, 5C, and 5D are diagrams showing composite materials having a photocatalytic thin film of the invention.
Figure 5B:
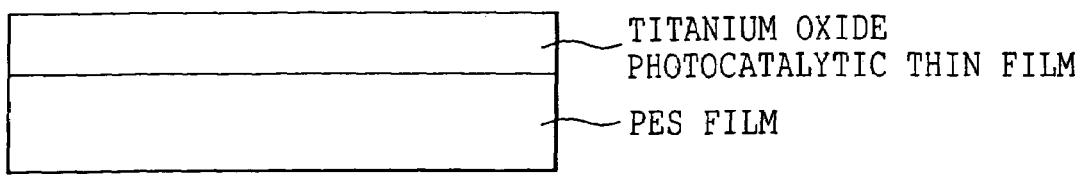
Figure 5C:
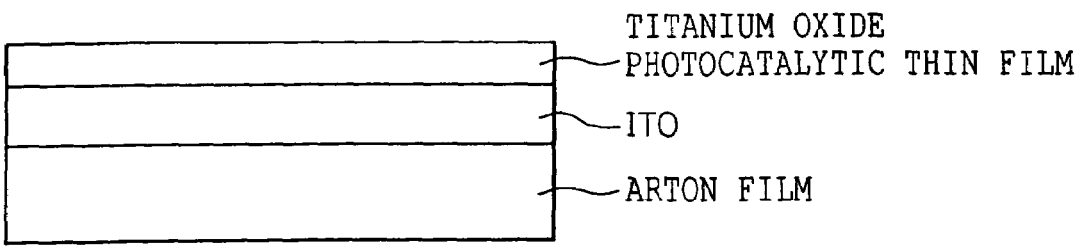
Figure 5D:
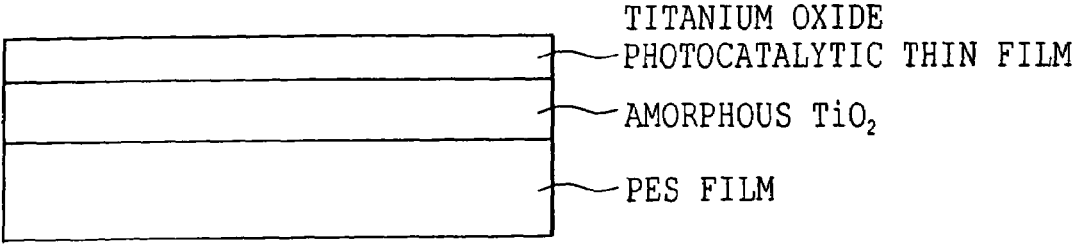

An example of the foregoing composite material is shown. FIG. 5A shows a composite material provided with a glass substrate (the thickness of 0.7 mm) and a titanium oxide photocatalytic thin film of a film thickness of 200 nm thereon and the titanium oxide film is made to have a thickness for suppressing reflection. FIG. 5B shows a composite material provided with a PES film (the thickness of 150 μm) and a titanium oxide photocatalytic thin film of a film thickness of 200 nm thereon. FIG. 5C shows a composite material provided with an Arton film (the thickness of 188 μm) and an ITO film with a film thickness of 75 nm as a protection film and also as a reflection prevention film and a titanium oxide photocatalytic thin film of a film thickness of 200 nm thereon. FIG. 5D shows a composite material provided with a PES film (the thickness of 0.15 mm) and an amorphous titanium oxide of a film thickness of 10 nm and a titanium oxide photocatalytic thin film of a film thickness of 200 nm thereon. These titanium oxide photocatalytic thin films have a refractive index of 2.5.

Next, one example of an experimental apparatus (hereinafter, in some cases referred to as an annealing apparatus) to be employed for the titanium oxide photocatalytic thin film production method of the invention will be described below.

FIG. 6 is a schematic conceptual diagram showing one example of an annealing apparatus for carrying out the treatment of the invention under the reductive gas atmosphere (heating and excimer beam radiation) and the annealing apparatus 29 has a chamber 21 for storing a base material bearing a titanium oxide thin film (hereinafter, in some cases referred to as a substrate), excimer beam radiation means 22, heating means 24, a heat transmission plate 26 for transmitting heat from the heating means, means for an ambient gas introduction and discharge which is not illustrated, an ambient gas introduction route 27, an ambient gas discharge route 28, and vacuum gas discharge means 40. The reference numeral 10 denotes a substrate provided with a base material and a titanium oxide thin film disposed thereon. Further, although it is not illustrated, temperature detection means is installed between the substrate 10 and the heat transmission plate 26 and by the unillustrated temperature detection means, the temperature of the substrate can be controlled. Further, at the time of using the apparatus, the oxygen partial pressure in the chamber is to be decreased and to decrease the oxygen partial pressure, it is possible to decrease the oxygen partial pressure by introducing a reductive gas for a prescribed time without using the vacuum discharge means and therefore, in such a case, no vacuum discharge means may be installed. As the excimer beam radiation means, an excimer lamp is preferable and as the heating means, a heater for heating electrically is preferable and also, as the heat transmission plate, for example, a heat transmissive ceramic plate is employed and as temperature detection means, for example, a thermocouple may be employed. As the vacuum gas discharge means, for example, a turbo molecular pump is employed.

Further, the foregoing chamber, in FIG. 6, may be a bell jar made of synthetic quartz and a jig to be put in the bell jar is preferably one made of synthetic quartz. Further, as a heater, a silicone rubber heater may be used. The foregoing synthetic quartz and silicone rubber heater can be used as a silicon-including compound in the production method of the invention.

In the case of using vacuum gas discharge means, the substrate 10 is put on the heat transmission plate 26 and after that, the chamber is evacuated to be vacuum once by the vacuum gas discharge means 40 to decrease the oxygen partial pressure in the inside. The heat transmission plate 26 is heated by the heating means 24 to increase the temperature of the substrate. When the substrate temperature reaches the treatment temperature of the invention, the reductive gas of such as hydrogen-nitrogen mixed gas and the like is introduced into an annealing apparatus and after the reductive gas is sufficiently passed, the excimer beam radiation is started.

Further, in the annealing apparatus in the case the photocatalytic thin film production of the invention is carried out under vacuum, in place of the ambient gas introduction and discharge means of the annealing apparatus in FIG. 6, vacuum gas discharge means for discharging the gas in the inside of the apparatus, for example, a turbo molecular pump may be installed.

Since it is possible to carry out low temperature annealing in the photocatalytic thin film production method of the invention, there is an advantage that no special heating means, temperature control means and the like are required to be employed and economical means may be used.

EXAMPLES

Hereinafter, the present invention will be described practically with reference to examples, however the invention is not at all limited to these examples.

Example 1

An anatase type titanium oxide with a film thickness of 200 nm was formed on a 0.7 mm-thick alkali-free glass substrate (Corning 1737 glass) at 250° C. substrate temperature by RF sputtering method. Next, using an experimental apparatus as illustrated in FIG. 6 (a bell jar of a capacity of about 1 L and made of synthetic quartz as a chamber and a jig in the bell jar is made of synthetic quartz and as a heater, a silicone rubber heater is used), after vacuum treatment ($10^{-2}$ Pa) was previously carried out to remove oxygen, under highly pure nitrogen gas atmosphere containing 3% of hydrogen gas (flow rate: 1 L/min, atmospheric pressure), the foregoing glass substrate on which the titanium oxide was formed was heated at 150° C. and while the temperature being kept, excimer beam (wavelength: 172 nm, beam intensity: 10 mW/cm$^2$) was radiated for 10 minutes by an excimer lamp (Ushio Inc.).

Figure 1B:
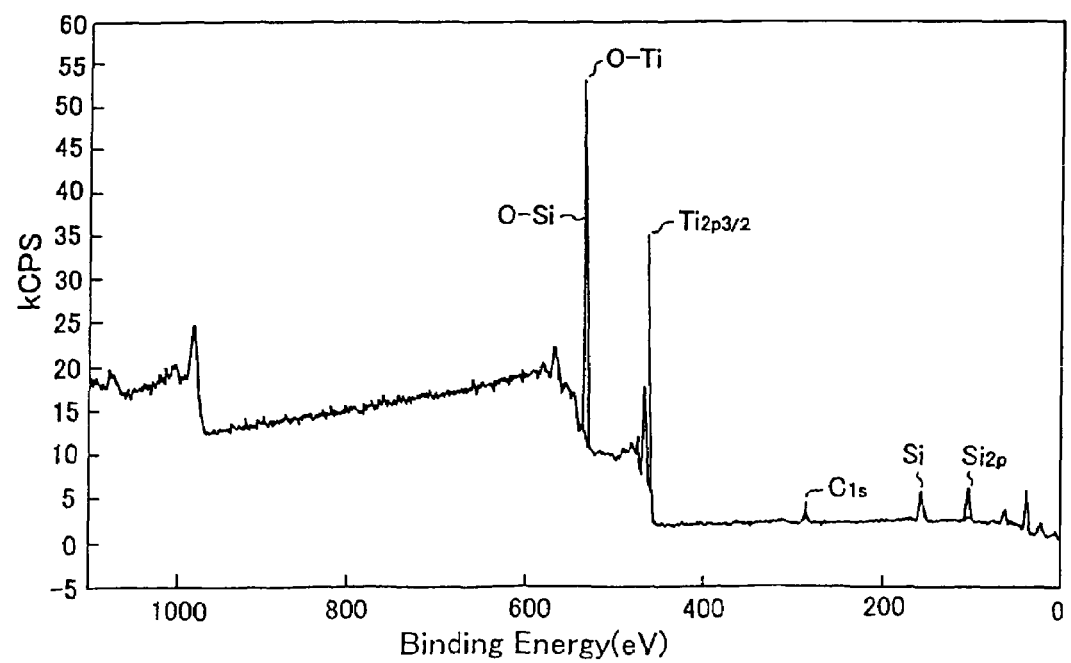
FIG. 1B is a graph showing an XPS measurement result of a titanium oxide thin film after the treatment.
Figure 2:
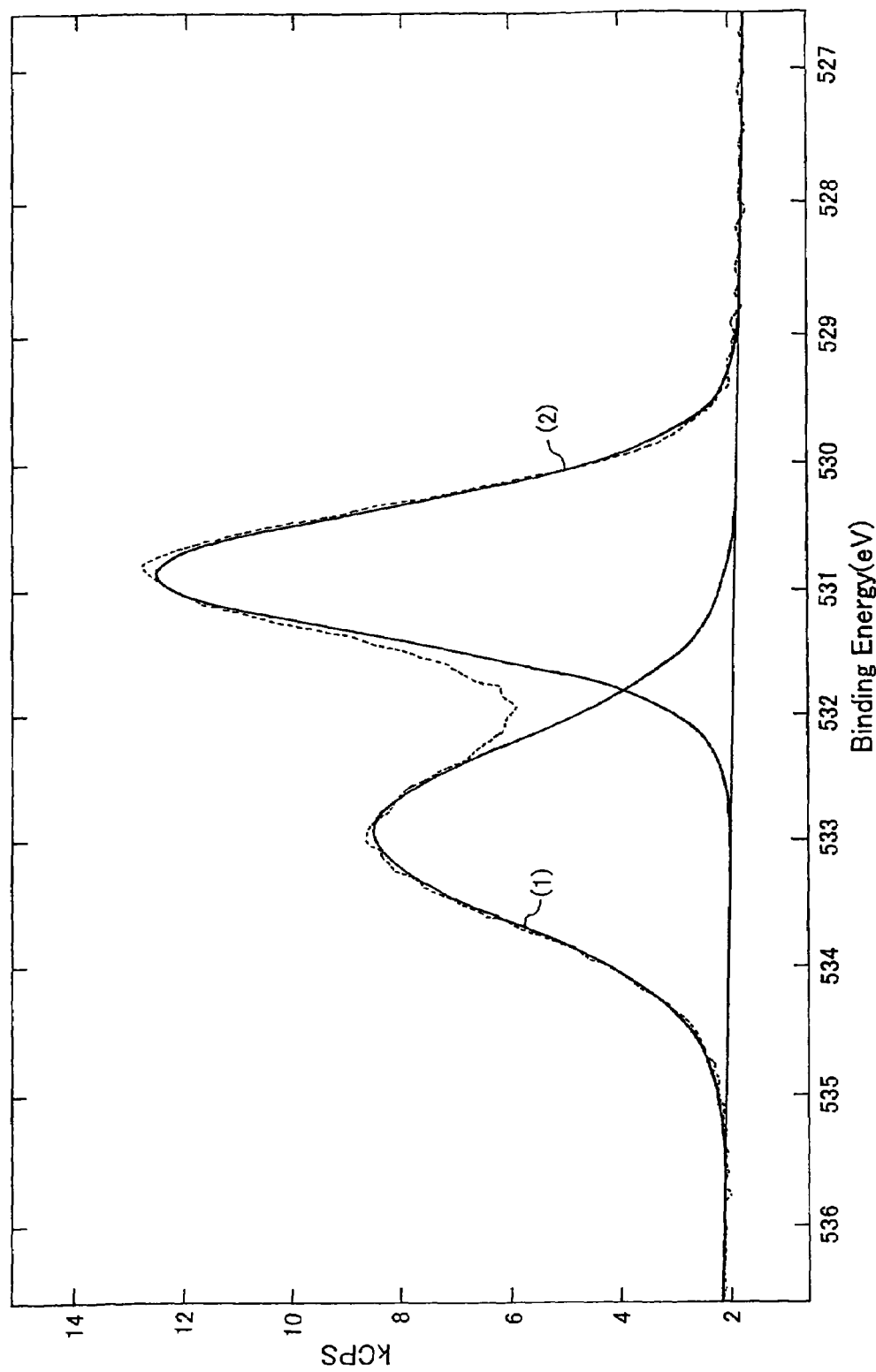
FIG. 2 is a graph of FIG. 1B in which the compounded peak of Ti—O and Si—O is separated into Ti—O and Si—O.
Figure 3:
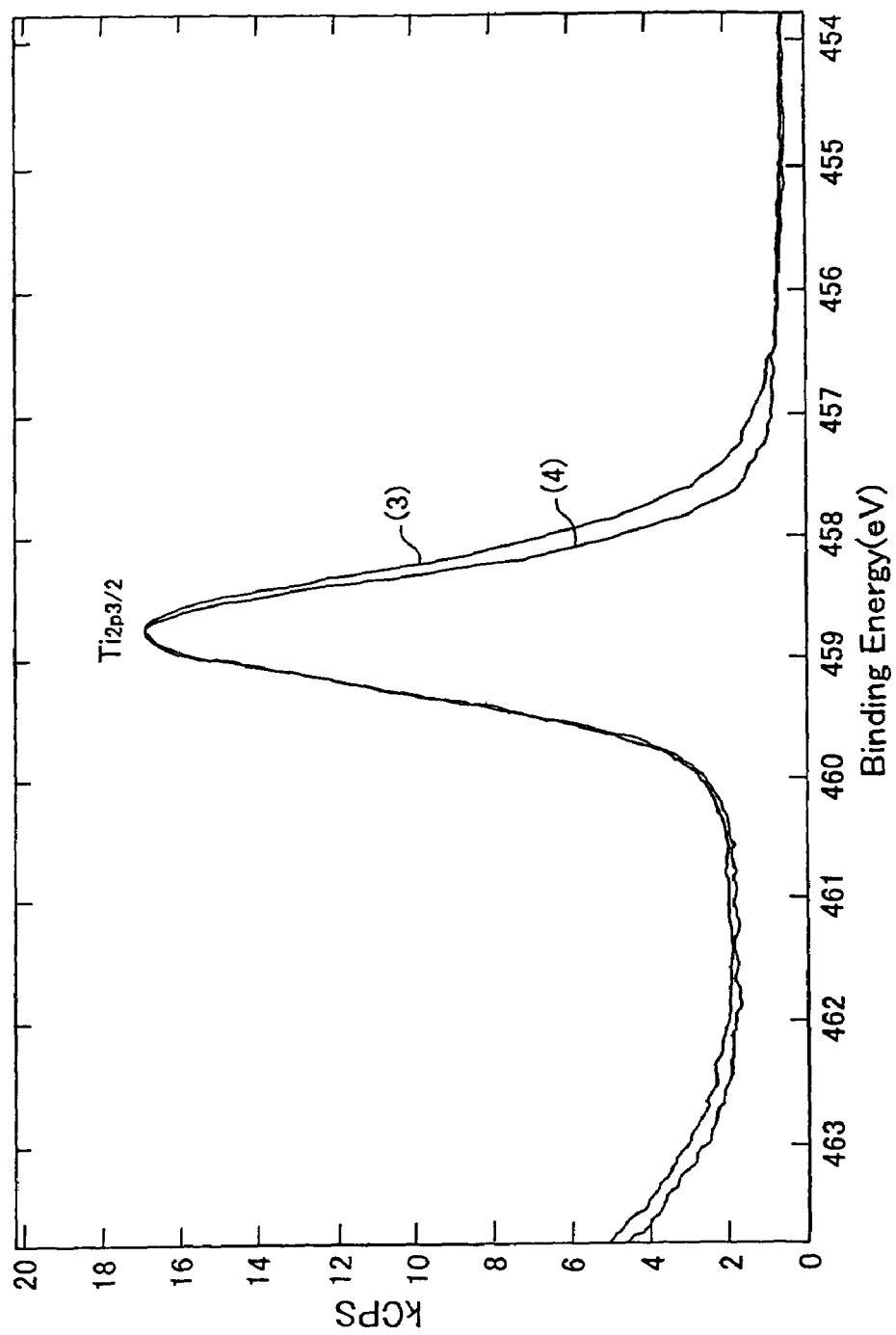
FIG. 3 is a magnified graph of $Ti_{2p3/2}$ of the XPS measurement result before and after the treatment of Example 1.

XPS analysis of the obtained thin film treated by excimer beam was carried out. FIGS. 1A and 1B show the XPS measurement results of a titanium oxide thin film before and after the treatment. FIG. 1A is the measurement result before treatment and the peak of O—Ti is observed. Further, FIG. 1B shows the measurement result after treatment and the peaks of O—Ti and O—Si are observed. Further, FIG. 2 shows the result of simulation treatment of FIG. 1B by separating the peaks of O—Ti and O—Si and the dotted line is the raw data and the curve (1) and the curve (2) show simulation lines of O—Si and O—Ti, respectively. Further, FIG. 3 shows the peak of $Ti_{2p3/2}$ of titanium dioxide before and after the treatment and the curve (3) shows that before treatment and the curve (4) shows that after treatment. As being understood from FIG. 3, it can be confirmed that crystallization is promoted by the treatment of the invention.

On the other hand, as a result of the peak separation analysis of the XPS analysis, the average of the mole ratio of Ti—O and Si—O from the surface to 5 nm of the obtained titanium oxide photocatalytic thin film was found 34:30. Further, in the portion deeper than the portion from the surface to 5 nm of the titanium oxide photocatalytic thin film, no Si—O was practically detected.

According to these facts, the surface layer of the photocatalytic thin film obtained in this example was found to be a hybrid layer containing titanium oxide and silicon oxide.

Figure 4:
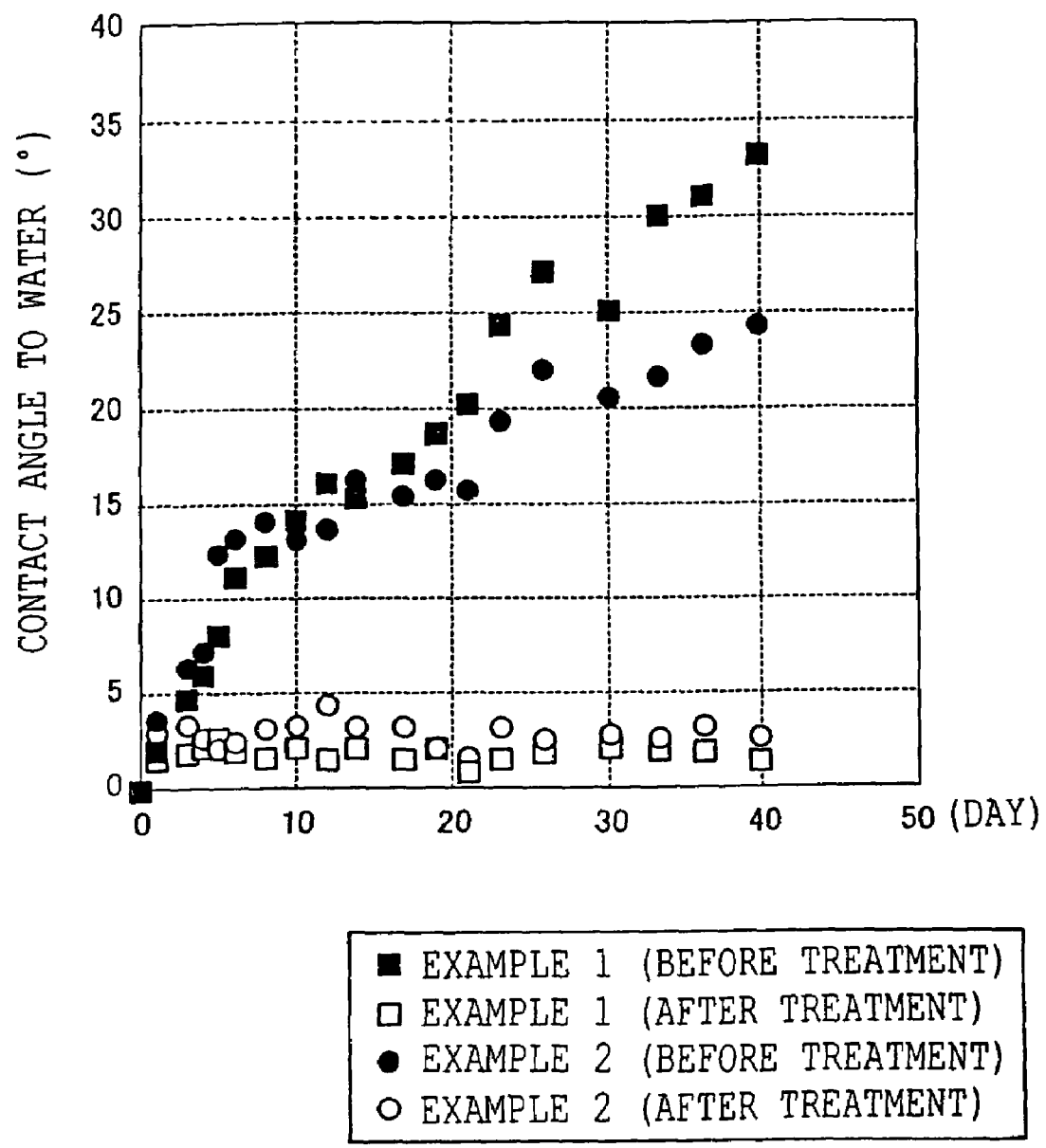
FIG. 4 is a graph showing a contact angle of the photocatalytic thin film to water with the lapse of time before and after the treatment in Example 1 and Example 2.

Further, the contact angle of the foregoing photocatalytic thin film to water in a dark place was investigated. It was maintained to be 5° or lower for at least 3 months. FIG. 4 shows the result together with the contact angle of the titanium oxide thin film before heating and excimer beam radiation treatment (in the figure, the result up to 40 days is shown).

As FIG. 4 shows, the result of the contact angle without treatment of the invention is found increased to 33° after 40 days, whereas it is kept 5° or lower by carrying out the treatment of the invention.

Further, in order to investigate the photocatalytic activity, the coloring material decomposition characteristic was investigated to find sufficient photocatalytic activity.

Example 2

An anatase type titanium oxide with a film thickness of 200 nm was formed at 150° C. substrate temperature by RF sputtering method after a 75 nm-thick ITO film was formed on a 0.15 mm-thick plastic sheet substrate (PES film produced by Sumitomo Bakelite Co., Ltd.). Next, using the same experimental apparatus as that of the Example 1, heating and excimer beam radiation was carried out in the same conditions as the Example 1, except that the heating temperature of the plastic sheet substrate was changed to be 130° C.

In the same manner as the Example 1, XPS analysis of the obtained excimer beam-treated thin film was carried out to find that a hybrid film of silicon oxide and titanium oxide is formed on the surface.

Further, as a result of investigation on the contact angle retention property of the foregoing photocatalytic thin film to water in a dark place, the contact angle was found kept at 5° or lower for at least 3 months. FIG. 4 shows the result together with the contact angle of the titanium oxide thin film before heating and excimer beam radiation treatment (in the figure, the result up to 40 days is shown). As FIG. 4 shows, the result of the contact angle without treatment of the invention is found increased to 33° after 40 days, whereas it is kept 5° or lower by carrying out the treatment of the invention.

Further, in order to investigate the photocatalytic activity, the coloring material decomposition characteristic was investigated to find sufficient photocatalytic activity.

Example 3

After a 75 nm-thick ITO film was disposed on a 188 μm thick Arton film substrate, an anatase type titanium oxide with a film thickness of 110 nm was formed at 150° C. substrate temperature by RF sputtering method. Next, using the same experimental apparatus as that of the Example 1, heating and excimer beam radiation was carried out in the same conditions as the Example 2.

In the same manner as the Example 1, XPS analysis of the obtained excimer beam-treated thin film, evaluation on the contact angle retention property in a dark place, and evaluation on the photocatalytic activity are carried out to find similar results as those of the Example 1.

Example 4

A 10 nm-thick amorphous titanium dioxide was formed without heating on a 0.15 mm-thick plastic sheet substrate (PES film produced by Sumitomo Bakelite Co., Ltd.) and then substrate temperature was risen to 150° C., an anatase type titanium oxide with a film thickness of 200 nm was formed by RF sputtering method.

Next, using the same experimental apparatus as that of the Example 1, heating and excimer beam radiation was carried out in the same conditions as the Example 1, except that the heating temperature of the plastic sheet substrate was changed to be 130° C.

In the same manner as the Example 1, XPS analysis of the obtained excimer beam-treated thin film, evaluation on the contact angle retention property in a dark place, and evaluation on the photocatalytic activity are carried out to find similar results as those of the Example 1.

Unlike a conventional titanium oxide film bearing a silica coating on the surface, the titanium oxide photocatalytic thin film of the invention does not cause photocatalytic activity deterioration even in the case it is kept in a dark place for a long term and a small contact angle to water can be maintained. Further, since the photocatalytic thin film of the invention has a high activity, sufficiently high photocatalytic activity can be obtained even if the film thickness is made thin. Accordingly, interference color of the light based on the high refractive index of titanium oxide can be eliminated and high transparency in a visible light range can be provided.

Further, the photocatalytic thin film production method of the invention has advantages that the treatment time is short and no large-scale apparatus is required, as compared with a conventional method.

What is claimed is:

1. A production method of a titanium oxide photocatalytic thin film comprising a surface layer including silicon oxide and titanium oxide, the production method comprising the steps of:
    forming an anatase type titanium oxide thin film on a substrate by a sputtering method, an RF sputtering method, an electron beam deposition method, or an ion plating method;
    adding the silicon oxide to the anatase type titanium oxide thin film by radiating excimer beam to the anatase type titanium oxide thin film while heating the substrate in the presence of a compound, which includes silicon, selected from the group consisting of quartz, silicone resin, silicone rubber, silicone oil, polysilane, and silane gas, thereby forming the surface layer including the titanium oxide and the silicon oxide,
    wherein the radiating of the excimer beam to the anatase type titanium oxide thin film is carried out in a vacuum or a gas atmosphere,
    at least the adding of silicon oxide to the anatase type titanium oxide thin film occurs in an annealing apparatus, and
    the compound, which includes silicon, is present in a member of the annealing apparatus and is not present in the substrate or any layer directly or indirectly formed on the substrate.

2. A production method of a titanium oxide photocatalytic thin film according to claim 1, wherein the compound, which includes silicon, is a compound containing —Si—O— bond.

3. A production method of a titanium oxide photocatalytic thin film according to claim 1, wherein the radiating of the excimer beam to the anatase type titanium oxide thin film is carried out in the gas atmosphere, which is one of a reductive gas atmosphere and a nitrogen gas atmosphere.

4. A production method of a titanium oxide photocatalytic thin film according to claim 1, wherein the heating temperature of the substrate is in a range from 50° C. to 300° C.

5. A production method of a titanium oxide photocatalytic thin film according to claim 1, wherein the heating temperature of the substrate is in a range from 50° C. to 230° C.

6. A production method of a titanium oxide photocatalytic thin film according to claim 1, wherein the substrate comprises a plastic substrate and the substrate heating temperature is in a range from 50° C. to the heat resistant temperature of the plastic substrate.

7. A production method of a titanium oxide photocatalytic thin film according to claim 1, further comprising disposing a reflection prevention film between the anatase type titanium oxide thin film and the substrate.

8. A production method of a titanium oxide photocatalytic thin film according to claim 7, wherein the reflection prevention film comprises an inorganic oxide thin film.

9. A production method of a titanium oxide photocatalytic thin film according to claim 7, wherein the refractive index of the reflection prevention film is within a range from 1.5 to 2.3.

10. A production method of a titanium oxide photocatalytic thin film according to claim 7,
    wherein the refractive index of the reflection prevention film is between the refractive index of the substrate and the refractive index of the titanium oxide photocatalytic thin film; and
    the optical film thickness, as expressed by a product of the film thickness and the refractive index of the reflection prevention film, is one of ¼ of a wavelength and a whole number multiple of ¼ of the wavelength, wherein the wavelength is in the vicinity of the center of the visible light range.

11. A production method of a titanium oxide photocatalytic thin film according to claim 7, wherein the optical film thickness of the reflection prevention film, as expressed by a product of the film thickness of the reflection prevention film and the refractive index of the reflection prevention film, is in a range from 110 nm to 160 nm or 330 nm to 480 nm.

12. A production method of a titanium oxide photocatalytic thin film according to claim 1, further comprising a step of disposing a protection film between the anatase type titanium oxide thin film and the substrate,
    wherein the substrate comprises a plastic substrate and the protection film protects the substrate from deterioration.

13. A production method of a titanium oxide photocatalytic thin film according to claim 12, wherein the protection film comprises an inorganic oxide thin film.

14. A production method of a titanium oxide photocatalytic thin film according to claim 13, wherein the inorganic oxide thin film is selected from a group consisting of an amorphous titanium oxide thin film, $SnO_2$ thin film, a $SiO_2$ thin film, and an ITO thin film.

15. A production method of a titanium oxide photocatalytic thin film according to claim 12, wherein the refractive index of the protection film is in a range from 1.4 to 2.3.

16. A production method of a titanium oxide photocatalytic thin film according to claim 12,
    wherein the refractive index of the protection film is between the refractive index of the substrate and the refractive index of the titanium oxide photocatalytic thin film; and
    the optical film thickness, as expressed by a product of the film thickness and the refractive index of the protection film, is one of ¼ of a wavelength and a whole number multiple of ¼ of the wavelength, wherein the wavelength is in the vicinity of the center of the visible light range.

17. A production method of a titanium oxide photocatalytic thin film according to claim 1, wherein
    the annealing apparatus comprises a chamber, a heating means, a heat transmission plate, a jig, and a gas atmosphere, and
    the compound, which includes silicon, is present in one of the group consisting of the chamber, the heating means, the heat transmission plate, the jig, and the gas atmosphere.

* * * * *